United States Patent

Verweij et al.

[11] 4,007,202
[45] Feb. 8, 1977

[54] AZETIDINE DERIVATIVES

[75] Inventors: Jan Verweij, Leiden; Hong Sheng Tan, Bleiswijk, both of Netherlands

[73] Assignee: Gist-Brocades N.V., Delft, Netherlands

[22] Filed: Feb. 7, 1975

[21] Appl. No.: 547,948

[30] Foreign Application Priority Data

Feb. 8, 1974 United Kingdom ............ 05811/74

[52] U.S. Cl. .................. 260/326 S; 260/239.1;
260/243 C; 260/260; 260/281 GP; 260/309.5;
260/326.37; 424/246
[51] Int. Cl.² ............. C07D 207/12; C07D 209/48
[58] Field of Search .................. 260/326 S, 326.37

[56] References Cited

UNITED STATES PATENTS 3,843,682  10/1974  Kukolja et al. ................. 260/326 S
3,880,880  5/1975  Ellis et al. ...................... 260/326 S Primary Examiner—Dolph H. Torrence
Attorney, Agent, or Firm—Hammond & Littell

[57] ABSTRACT

Novel azetidine derivatives of the formula

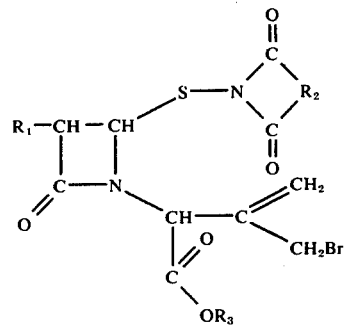

wherein $R_1$ is an acylamido group, $R_2$ is selected from the group consisting of

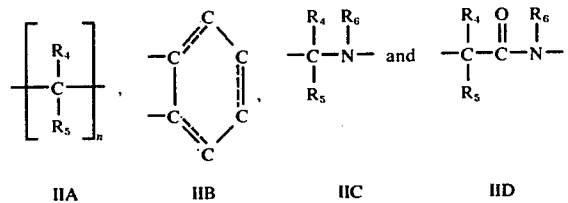

IIA  IIB  IIC  IID wherein $R_4$, $R_5$ and $R_6$ are individually selected from the group consisting of hydrogen, lower alkyl and lower alkenyl, n is 2 or 3 and — in the case when formula IIB is a phenyl - this group may carry one to four substituents selected from the group consisting of halogen, lower alkyl, lower alkenyl and phenyl, and $R_3$ is lower alkyl optionally substituted with 1 or 2 phenyls which phenyl groups may be substituted with nitro and the dotted lines of formula IIB indicate the optional presence of double bonds and a process for their preparation and process for the preparation of cephalosporanic acid derivatives using the azetidines of formula I as intermediates.

10 Claims, No Drawings

AZETIDINE DERIVATIVES

STATE OF THE ART

Various attempts have been made to introduce a functional group or atom in the methyl group of 2-methylpropenyl such as -CR=C(CH₃)-CH₃ where R is an esterified carboxy group which side chains are attached to the nitrogen atom of azetidin-2-ones having also a 4-thio-side chain [Brain et al, J.C.S. Chem. Comm., p 229-230, 1972]. These attempts did not result in the desired functionalized derivatives apparently due to the inertness of the allylic methyl group in the said side chain. Investigations for azetidin-2-ones with functionalized methyl groups in a propenyl side chain have been going on for some time as such compounds would be valuable intermediates in processes for preparing other fused β-lactams and/or cephalosporanic acid derivatives.

OBJECTS OF THE INVENTION

It is an object of the invention to provide the novel azetidine derivatives of the formula I.

It is another object of the invention to provide a novel process for the preparation of the azetidine compounds of formula I.

It is a further object of the invention to provide a novel process for the preparation of cephalosporanic acid derivatives starting from the azetidines of formula I.

These and other objects and advantages of the invention will become obvious from the following detailed description.

THE INVENTION

The novel azetidines of the invention have the formula

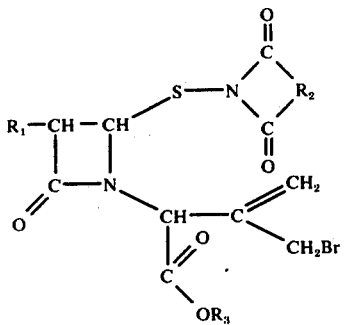

wherein R₁ is an acylamido group, R₂ is selected from the group consisting of

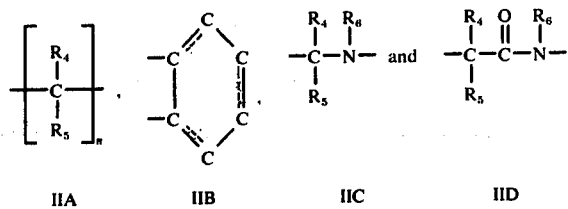

wherein R₄, R₅ and R₆ are individually selected from the group consisting of hydrogen, lower alkyl and lower alkenyl, n is 2 or 3 and — in the case when formula IIB is a phenyl — this group may carry one to four substituents selected from the group consisting of halogen, lower alkyl, lower alkenyl and phenyl, and R₃ is lower alkyl optionally substituted with 1 or 2 phenyls which phenyl groups may be substituted with nitro and the dotted lines of formula IIB indicate the optional presence of double bonds The term "acylamido" is meant any group known to those skilled in the art in both natural and synthetic penicillins and, more particularly, the acylamido groups which are the 6β-side chains in penicillins that can be obtained by fermentation procedures. Preferably, R₁ is phenylacetamido or phenoxyacetamido. The terms "lower alkyl" and "lower alkenyl" as employed herein, alone or in conjunction with other designated groups, is meant straight- or branched-chain alkyl and alkenyl groups containing at most four carbon atoms. The halogen atoms referred to may be chlorine, bromine, iodine or fluorine.

Preferably, R₄, R₅ and R₆ in formulae IIA to IID are hydrogen or methyl or ethyl. Suitable groups represented by the formula

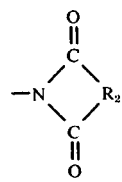

in the azetidine derivatives of formula I are, for example, hexahydrophthalimido, 1,5,5-trimethylhydantoin-3-yl, 3,3-dimethylglutarimido, 3-ethyl-3-methylglutarimido and 5-ethyl-1-methyl-5-phenyl-2,4,6-trioxo-hexahydropyrimidin-3-yl and preferably, succinimido or phthalimido. R₃ preferably is selected from the group consisting of methyl, butyl, diphenylmethyl and p-nitrobenzyl.

The novel process of the invention for the preparation of the compounds of formula I comprises allylic bromination of an azetidine compound of the formula

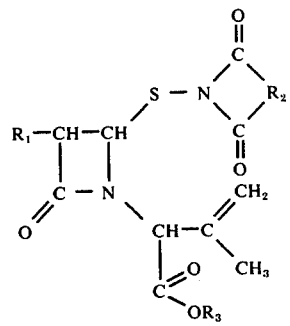

wherein R₁, R₂ and R₃ are as defined above. The allylic bromination can be effected by reacting an azetidine derivative of formula III with known brominating agents under reaction conditions which favor activation of the bromination agent. Suitable bromination agents are, for example, N-bromo-imides such as 1,3-dibromo-5,5-di(lower alkyl)hydantoins (for example 1,3-dibromo-5,5-dimethylhydantoin, 1,3-dibromo-5-ethyl-5-methylhydantoin and 1,3-dibromo-5-isopropyl-5-methylhydantoin), N-bromo-succinimide and N-bromo-phthalimide. Preferred bromination agents are 1,3-dibromo-5,5-dimethylhydantoin and N-bromosuccinimide.

The necessary activation of the bromination agent can be achieved by adding a free radical initiator to the reaction mixture. Examples of suitable initiators are azo-compounds such as azo-isobutyronitrile, and peroxides such as benzoyl peroxide. The activation of the bromination agent can also be effected by irradiation of the reaction mixture with ultra-violet or visible light. When a free radical initiator is used for the activation of the bromination agent, the reaction is advantageously carried out at a temperature between 40° and 90° C., the lower limit of this range being determined by the minimum temperature which is necessary for the initiator to start its action. In the case when the activation is effected by irradiation of the reaction mixture, the temperature preferably is between −20° and 30° C.

The reaction is preferably carried out in an inert organic medium in which the azetidine starting material of formula III should be soluble at least to some extent. Examples of suitable solvents are chlorinated hydrocarbons such as chloroform, methylene chloride, and 1,2-dichloroethane and benzene. Advantageously, propyleneoxide is added to the reaction mixture.

The azetidine derivatives of formula I obtained by the process may be separated from the reaction mixture by application of known procedures. For example, the reaction mixture may be evaporated to dryness and the azetidine derivative obtained from the residue by chromatography on silica gel.

The azetidine derivatives of formula III employed as starting materials in this process of the invention, as well as methods for their preparation, have been disclosed in commonly assigned, copending U.S. patent application Ser. No. 440,725 filed Feb. 8, 1974 by reacting a corresponding penicillanic S(β)- or R(α)-sulfoxide of the formula

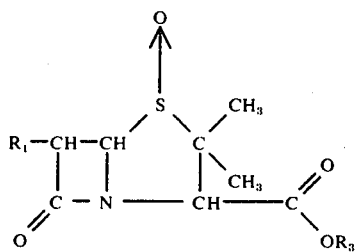

IVA or

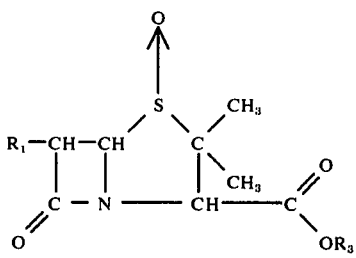

IVB wherein $R_1$ and $R_3$ are as hereinbefore defined with a silicon-containing compound of the formula

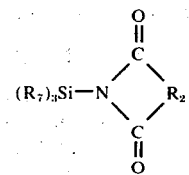

wherein $R_2$ is as hereinbefore defined, and the symbols $R_7$ are the same or different and each represents a lower alkyl or alkoxy optionally substituted by halogen, or a phenyl group under anhydrous conditions, in an inert organic solvent at temperatures between 50° and 180° C.

Preferably, the silicon-containing compound of formula V is employed in a molar excess in relation to the amount of sulfoxide of formula IV A or B. Suitable solvents are, for example, N-acetylsuccinimide, N-acetylphthalimide, dimethylacetamide and dimethylformamide. Advantageously, acetic acid or trimethylsilyl acetate is added to the reaction mixture.

The azetidine derivatives of formula I are useful as intermediates in a new process for the preparation of cephalosporanic acid derivatives which is another feature of the invention. The said new process is useful for preparing cephalosporanic acid derivatives of the formula

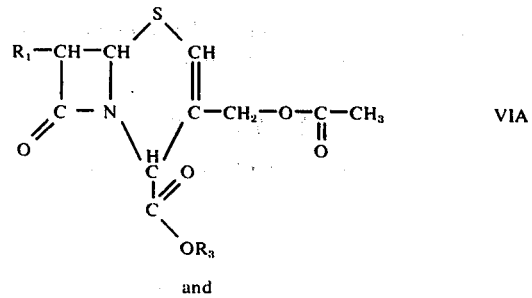

VIA and

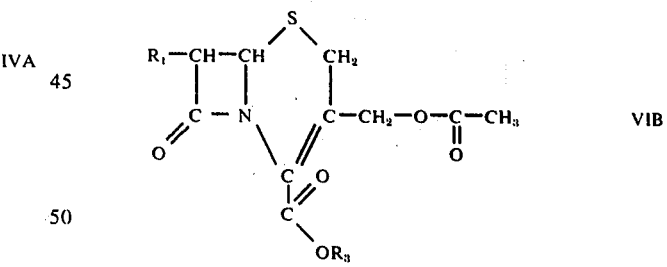

VIB wherein $R_1$ and $R_3$ are as hereinbefore defined by reacting an azetidine derivative of formula I with an alkali metal, preferably potassium, ammonium or tetra(lower alkyl)ammonium acetate in an inert organic medium. The rection is carried out at a temperature between −20° and 80° C. Suitable solvents are, for example, acetone and dimethylformamide. In some cases, it is advantageous to add acetic acid to the reaction mixture.

Usually there is obtained a mixture of $\Delta^2$- and $\Delta^3$-cephalosporanic acid derivatives of formulae VIA and VIB. The $\Delta^2$- and $\Delta^3$-isomers may be obtained separately from the reaction mixture by means of chromatography on silica gel. If desired, the $\Delta^2$-cephalosporanic acid derivatives of formula VIA may be converted in manner known per se into the corresponding Δ³-isomers of formula VIB.

The cephalosporanic acid derivatives of formula VI, especially the Δ³-isomers of formula VIB, are known to have valuable antibacterial properties which make them useful in the treatment of infections caused by pathogenic bacteria, some of which are resistant to other antibiotics. The processes of this invention now provide a new route to this group of therapeutically interesting cephalosporin derivatives, starting from the readily available penicillanic sulfoxides of formula IVA and B, via the azetidine derivatives of formula I.

In the following examples there are described several preferred embodiments to illustrate the invention. However, it should be understood that the invention is not intended to be limited to the specific examples. Unless indicated otherwise, the PMR spectra were recorded on a Varian A 60 instrument for solutions in deuterochloroform containing tetramethylsilane as internal reference and the δ-values are given in ppm.

EXAMPLE 1

1-(1-methoxycarbonyl-2-bromomethylprop-2-enyl)-3-phenyl-acetamido-4-succinimidothio-azetidin-2-one

STEP A 780 ml (6.1 moles) of trimethylchlorosilane were added with vigorous stirring over 2 hours to a mixture of 400 g (4 moles) of succinimide, 900 ml (6.5 moles) of triethylamine and 2700 ml of toluene and the mixture was refluxed with stirring for one hour and was then cooled to room temperature. The mixture was filtered and the filter was washed with one liter of toluene and one liter of petroleum ether (b.p = 40°–60° C). The combined filtrate and washings were concentrated to 700 ml and then distilled at reduced pressure to 573 g (3.4 moles — 84% yield) of N-trimethylsilyl succinimide with a boiling point of 62° C at 0.33 mm Hg.

PMR ($CCl_4$): 0.38 (s, 9); 2.62 (s, 4).

IR ($CCl_4$): 1770, about 1705, 1325, 1253 and 850 $cm^{-1}$.

STEP B

A mixture of 25.5 g (70 mmoles) of the methyl ester of benzylpenicillin-S-sulfoxide, 410 ml of dimethylacetamide, 56 ml (340 mmoles) of N-trimethylsilyl succinimide and 1.8 ml of acetic acid was stirred for 3.5 hours at 105° C and after cooling to room temperature, the mixture was poured into a cold mixture of 500 ml of ethyl acetate and 1500 ml of water. The organic layer was separated and the aqueous layer was extracted twice with 250 ml portions of ethyl acetate. The combined extracts were washed with water, dried over magnesium sulfate and treated with charcoal. After filtration, the solution was evaporated to dryness and the residue was treated with carbon tetrachloride. The residue was filtered off, washed with diethyl ether and dried to obtain 19 g (42.7 mmoles or 61%) of 1-(1-methoxycarbonyl-2-methylprop-2-enyl)-3-phenylacetamido-4-succinimidothio-azetidin-2-one.

PMR: 1.87 (s, 3); 2.81 (s, 4); 3.69 (s, 2); 3.76 (s, 3); 4.67 (s, 1); 5.08 (centre of ABq; 2); 5.11 (d, 1; J=4.5 Hz); 5.35 (dd, 1; J=4.5 Hz and J=8.5 Hz); 7.33 (s, 5); 7.48 (d, 1; J= 8.5 Hz).

IR (KBr): 3300, 3085, 3065, 3032, 1775, 1720, 1670–1650 and 1520 $cm^{-1}$.

STEP C 50 ml (714 mmoles) of propylene oxide, 18 g (112 mmoles) of N-bromosuccinimide and 0.25 g (1.5 mmole) of azoisobutyronitrile were added to a solution of 22.5 g (51 mmoles) of 1-(1-methoxycarbonyl-2-methylprop-2-enyl)-3-phenylacetamido-4-succinimidothio-azetidin-2-one in 1.5 liters of dry 1,2-dichloroethane and the mixture was refluxed in the dark under a nitrogen atmosphere for 4 hours. The mixture was washed twice with a sodium metabisulfite solution and three times with water. The solvent was removed in vacuo and the residue was dissolved in 300 ml of ethyl acetate. The solution was treated with decolorizing charcoal, and after concentrating the resulting solution to 50 ml and adding tetrahydrofuran and diethyl ether, 20 g of a precipitate was obtained. 0.5 g of this crude material was purified twice by column chromatography (silica gel, 4:1 (v/v) toluene-ethyl acetate; silica gel, 5:1 (v/v) benzene-acetone) to obtain 45 mg of 1-(1-methoxycarbonyl-2-bromomethylprop-2-enyl)-3-phenylacetamido-4-succinimidothio-azetidin-2-one.

PMR: (220 Mc) 2.78 (s, 4); 3.66 (s, 2); 3.74 (s, 3); 4.12 (s, 2); 5.00 (s, 1); 5.12 (d, 1; J=4.5 Hz); 5.20 (dd, 1; J=4.5 Hz and J=9 Hz); 5.32 (s, 1); 5.54 (s, 1); ca 7.30 (m,5).

IR (KBr): 3350, 1780, 1725, 1670, 1525, 1300, 1250 and 1150$cm^{-1}$.

EXAMPLE 2

1-(1-methoxycarbonyl-2-bromomethylprop-2-enyl)-3-phenylacetamido-4-succinimidothio-azetidin-2-one

STEP A

A mixture of 25 g (71 mmoles) of benzylpenicillin-S-sulfoxide, 250 ml of dimethylacetamide and 75 ml (460 mmoles) of N-trimethylsilylsuccinimide was stirred for 4 hours at 105° C and the solvent was removed by evaporation in vacuo. The residue was dissolved in 250 ml of ethyl acetate and rapidly washed twice with 125 ml of an acetic acid 4NHCL solution of pH 1.8. The solution was dried over magnesium sulfate, treated with charcoal and after the addition of 500 ml of toluene, concentrated to a small volume. Trituration with diethyl ether and n-hexane yielded 15 g of 1-(1-carboxy-2-methylprop-2-enyl)-3-phenylacetamido-4-succinimidothio-azetidin-2-one with a purity of 70% as estimated by PMR, using 2,6-dichloroacetophenone as internal standard. Thus the yield of pure azetidinone was 10.5 g (24.3 mmoles) or 34%.

STEP B 1-(1-carboxy-2-methylprop-2-enyl)-3-phenylacetamido-4-succinimidothio-azetidin-2-one was treated with a diazomethane solution in diethyl ether and after evaporation of the reaction mixture to dryness, the residue was purified by column chromatography on silica gel using a 5:3 (v/v) mixture of toluene and ethyl acetate, and finally only ethyl acetate, as an eluent. The structure of 1-(1-methoxycarbonyl-2-methylprop-2-enyl)-3-phenylacetamido-4-succinimidothio-azetidin-2-one so obtained was confirmed by mass-spectrometry and PMR and IR spectroscopy.

PMR: 1.87 (s, 3); 2.80 (s, 4); 3.68 (s, 2); 3.75 (s, 3); 4.66 (s, 1); 5.03 (s, 1); 5.12 (s, 1); 5.12 (s, 1); 5.12 (d, 1; J=4.5 Hz); 5.38 (dd, 1; J=4.5 and 8.5 Hz); 7.29 (s, 5); 7.33 (d, 1; J=8.5 Hz).

IR(KBr): 3300, 3085, 3065, 3032, 1775, 1720, 1670–1650, 1520cm⁻¹.

STEP C 1.4 g (8 mmoles) of N-bromosuccinimide were added to a solution of 2.7 g (6 mmoles) of 1-(1-methoxycarbonyl-2-methylprop-2-enyl)-3-phenylacetamido-4-succinimidothio-azetidin-2-one in 450 ml of 1,2-dichloroethane and the mixture was irradiated under nitrogen for 75 minutes at 15° C with a Hanovia TQ 150 mercury high pressure lamp using a Pyrex filter. After washing twice with water, drying and treating with decolorizing charcoal, the reaction mixture was concentrated. The precipitate was chromatographed on silica gel (benzene-tetrahydrofuran 4:1 (v/v)) to obtain 600 mg (1.1 mmole) of 1-(1-methoxycarbonyl-2-bromomethylprop-2-enyl-3-phenylacetamido-4-succinimidothio-azetidin-2-one. The structure was confirmed by PMR and IR spectroscopy.

EXAMPLE 3

1-(1-methoxycarbonyl-2-bromomethylprop-2-enyl)-3-phenylacetamido-4-succinimidothio-azetidin-2-one

STEP A

A mixture of 25.5 g (70 mmoles) of the methyl ester of benzylpenicillin-S-sulfoxide, 410 ml of dimethylacetamide, 56 ml (340 mmoles) of N-trimethylsilylsuccinimide and 1.8 ml of acetic acid was stirred for 3.5 hours at 105° C and after cooling to room temperature, the reaction mixture was poured into a cold mixture of 500 ml of ethyl acetate and 1500 ml of water. The organic layer was separated and the aqueous layer extracted twice with 250 ml portions of ethyl acetate. The combined extracts were washed with water, dried over magnesium sulfate and treated with charcoal. After filtration, the solution was evaporated to dryness and the residue was triturated with carbon tetrachloride. The residue was filtered off, washed with diethyl ether and dried to obtain 19 g (42.7 mmoles or 61% yield) of 1-(1-methoxycarbonyl-2-methylprop-2-enyl)-3-phenylacetamido-4-succinimidothio-azetidin-2-one. The structure was confirmed by PMR spectroscopy.

STEP B

A mixture of 4.45 g (10 mmoles) of 1-(1-methoxycarbonyl-2-methylprop-2-enyl)-3-phenylacetamido-4-succinimidothio-azetidin-2-one, 10 ml of propylene oxide, 3.6 g (20 mmoles) of N-bromosuccinimide, 50 mg of azo-isobutyronitrile, 100 ml of 1,2dichloroethane and 200 ml of carbon tetrachloride was heated for 5 hours at 76° C under nitrogen. After washing with sodium metabisulfite and water, the reaction mixture was concentrated and purified by column chromatography [silica gel; toluene-ethyl acetate 3:1 (v/v)] to obtain 1-(1-methoxycarbonyl-2-bromomethylprop-2-enyl)-3-phenylacetamido-4-succinimidothio-azetidin-2-one. The structure was confirmed by PMR and IR spectroscopy.

EXAMPLE 4

1-(1-methoxycarbonyl-2-bromomethylprop-2-enyl)-3-phenylacetamido-4-phthalimidothio-azetidin-2-one

STEP A 250 g (1.7 moles) of phthalimide were suspended in 2.75 liter of acetonitrile and after 250 ml (1.8 moles) of triethylamine were added, the mixture was heated to gentle reflux 250 ml (1.97 moles) of trimethylchlorosilane were added in 10 minutes and the reaction mixture was then concentrated to a thick paste. 2.5 liter of light petroleum (80°–110° C) were added, the triethylammonium hydrochloride was filtered off and washed with 500 ml of light petroleum. The filtrate and washings were combined and concentrated until crystallization started. After cooling in the refrigerator for several hours, N-trimethylsilylphthalimide was isolated by filtration, washed with a small portion of light petroleum (40°–60° C) and dried in vacuo. The compound was further purified by recrystallization from ligroin (80°–100° C).

PMR: 0.51 (s, 9); 7.73 (centre of super imposed signals, 4).

STEP B

A mixture of 35 g (0.10 moles) of benzylpenicillin-S-sulfoxide, 125 g (0.57 mole) of N-trimethylsilylphthalimide, 260 ml of dimethylacetamide and 15 ml (0.1 mole) of trimethylsilyl acetate was heated with stirring for 3.5 hours at 105° C. The reaction mixture was cooled to room temperature and concentrated in vacuo at 40° C and 1 mm Hg. The residue was treated with 100 ml of toluene and was evaporated to dryness. A mixture of 250 ml of ethyl acetate, 200 ml of water and 50 g of crushed ice was added to the residue. The pH was adjusted to 1.8 by addition of 4 N hydrochloric acid and after stirring vigorously for 15 minutes at 0° C, the mixture was filtered to remove some phthalimide. The organic layer was separated, washed with cold 0.02 N hydrochloric acid, treated with charcoal, dried with magnesium sulfate, evporated to dryness and the residue was triturated with ethyl acetate. The precipitated phthalimide was removed by filtration and was washed with a small volume of ethyl acetate. The filtrate and washing were combined, concentrated to a small volume and upon cooling in the refrigerator, an additional amount of phthalimide precipitated which was removed by filtration and washed with a small volume of cold ethyl acetate. Upon evaporating of the combined filtrate to dryness and washing, there was obtained 1-(1-carboxy-2-methylprop-2-enyl)-3-phenylacetamido-4-phthalimidothio-azetidin-2-one. The yield was 46 g with a purity of 70% as estimated by PMR using 2,6-dichloroacetophenone as internal standard or the yield of pure azetidinone was 32 g (67 mmoles ) or 67%.

PMR: 1.89 (s, 3); 3.72 (s, 2); 4.87 (s, 1); 5.08 (broad s, 2); 5.10 (d, 1; J=4.5 Hz); 5.30 (dd, 1; J=4.5 Hz and 8.5 Hz); about 7.25 (super imposed signals, 7); 7.46 (d, 1; J= 8.5 Hz); 7.74 (broad s, 2).

IR (KBr): 3300, 3085, 3030, 1770, 1740, 1712, 1665, 1600 and 1530 cm⁻¹.

STEP C 14 g (purity 70%; 20 mmoles) of 1-(1-carboxy-2-methylprop-2-enyl)-3-phenylacetamido-4-phthalimidothio-azetidin-2-one was treated with a diazomethane solution in diethyl ether. After evaporation of the reaction mixture to dryness, benzene was added. After filtering off the phthalimide, the filtrate was concentrated and chromatographed [silica gel; toluene - ethyl acetate 4:1(v/v] to obtain 6.24 g (62% yield) of 1-(1-methoxycarbonyl-2-methylprop-2-enyl)-3-phenylacetamido-4-phthalimidothio-azetidin-2-one.

PMR: 1.91 (s, 3); 3.51 (s, 3); 3.77 (s, 2); 4.77 (s, 1); 5.05 (s, 1); 5.14 (s, 1); 5.13 (d, 1; J=4.5 Hz); 5.40 (dd, 1; J= 4.5 Hz and 8.5 Hz); 7.30 (s, 2); 7.83 (s, 2); 7.33 (s, 5); 7.38 (d, 1; J=8.5 Hz).

IR (KBr): about 3310, 1780, 1740, 1720, 1665 and 1610 cm$^{-1}$. M.S.: M$^+$ 493

STEP D

A mixture of 1.48 g (3 mmoles) of 1-(1-methoxycarbonyl-2-methylprop-2-enyl)-3-phenylacetamido-4-phthalimidothioazetidin-2-one, 1.22 g (6.9 mmoles) of N-bromosuccinimide and 225 ml of 1,2-dichloroethane was irradiated under nitrogen for 3.5 hours at 14° C with a Hanovia TQ 150 mercury high pressure lamp using a Pyrex filter. After washing twice with a 0.2 molar aqueous solution of sodium acetate and acetic acid buffered to pH 4.6, drying and treating with decolorizing charcoal, the reaction mixture was concentrated. The residue was then diluted with 10 ml of ethyl acetate and 10 ml of tetrahydrofuran and treated with n-hexane. The precipiate so obtained was filtered off and dried, to obtain 1.3 g of crude material which showed virtually one spot on TLC. This product was purified with column chromatography [silica gel; methylene chloride-ethyl acetate 9:1 (v/v)] to obtain 250 mg (0.5 mmole) of 1-(1-methoxycarbonyl-2-bromomethylpropyl-2-enyl)-3-phenylacetamido-4-phthalimidothioazetidin-2-one.

PMR: 3.56 (s, 3); 3.76 (s, 2); 4.19 (s, 2); 5.16 (d, 1: J= 4.5 Hz); 5.20 (s, 1); 5.28 (dd, 1; J= 4.5 Hz and 9.5 Hz); 5.40 (s, 1) and 5.62 (s, 1); 7.30 (d, 1; J=9.5 Hz); 7.37 (s, br, 5); 7.86 (s, br, 4).

IR (KBr): 3300, 1795, 1750, 1710, 1670, 1530, 1290, 1220, 1060 and 940 cm$^{-1}$.

EXAMPLE 5

1-(1-methoxycarbonyl-2-bromomethylprop-2-enyl)-3-phenylacetamido-4-phthalimidothio-azetidin-2-one A mixture of 381 g (1.1 mole) of benzylpenicillin-S-sulfoxide, 1608 g (7.3 moles) of N-trimethylsilylphthalimide and 2830 ml of dimethylacetamide was heated at 105° C during 5 hours and after cooling the reaction mixture was poured into a mixture of 6000 g of ice, 4000 ml of ethyl acetate and 60 ml of 2 N hydrochloric acid. After adjusting the pH with 2 N hydrochloric acid to 1.8 and stirring the mixture for 15 minutes, phthalimide was filtered off. After separating the layers, the ethyl acetate layer was washed with water, treated with charcoal and dried. After concentrating the ethyl acetate solution to about 2000 ml, standing overnight at 0° C, the solution was filtered and evaporated to dryness to obtain 485 g of crude product.

This material was recrystallized twice from dimethylformamide-toluene and 1,2-dichloroethane-carbon tetrachloride to obtain 210 g (0.44 mole) of 1-(1-carboxy-2-methylprop-2-enyl)-3-phenylacetamido-4-phthalimidothio-azetidin-2-one. This compound was converted by the procedure of Steps B, C and D of Example 4 into 1-(1-methoxycarbonyl-2-bromomethylprop-2-enyl)-3-phenylacetamido-4-phthalimidothio-azetidin-2-one.

EXAMPLE 6

1-(1-methoxycarbonyl-2-bromomethylprop-2-enyl)-3-phenoxyacetamido-4-phthalimidothio-azetidin-2-one

STEP A

A mixture of 180 g (491 mmoles) of phenoxymethylpenicillin-S-sulfoxide, 442 g (2015 mmoles) of N-trimethylsilylphthalimide, 10 ml of trimethylsilylacetate and 600 ml of dimethylacetamide was stirred for 7 hours at 104° C and after cooling to room temperature, the reaction mixture was poured into a mixture of 3 liters of ice water and 2 liters of ethyl acetate. The pH was adjusted to 2 by addition of 4 N hydrochloric acid and after stirring vigorously for 15 minutes, the mixture was filtered to remove phthalimide. The organic layer was separated, washed twice with 2 liters of water and concentrated to about 800 ml while acetone was being added. After filtering off more precipitated phthalimide, 250 ml of methyl isobutyl ketone were added to the filtrate and the filtrate was concentrated in vacuo. After standing overnight at 0° C, the formed crystalline precipitate were filtered off and dissolved in 1 liter of acetone. This solution was treated with charcoal, concentrated, and treated with methyl isobutyl ketone to remove some phthalimide. The filtrate was then concentrated to a small volume, treated with benzene and diethyl ether in order to precipitate the first crop of the desired product. A second crop was obtained from the mother liquor by adding some water. The total amount of crude material was then crystallized twice in the following manner: The azetidinone was dissolved in 200 ml of acetic acid and treated with charcoal. After adding 5 ml of water and 1.5 liter of hot benzene, the solution was stirred to obtain fine crystalline 1-(1-carboxy-2-methylprop-2-enyl)-3-phenoxyacetamido-4-phthalimidothio-azetidin-2-one which after drying weighed 152 g (62%). Dibs. p.: 148°–151° C.

PMR (CDCl$_3$ and 2 drops of DMSO-d 6): 1.98 (s, 3); 4.67 (s, 2); 4.85 (s, 1); 5.14 (s, br, 2); 5.24 (d, 1; J=4.5 Hz); 5.52 (dd, 1; J= 4.5 Hz and 8.5 Hz); 6.86 – 746 (m, 5); 7.43 (s, 1); 7.82 (s, br, 4); 8.33 (d, 1; J=8.5 Hz).

IR (KBr): 3350, 1785, 1760, 1740, 1710, 1670 and 1290 cm$^{-1}$.

STEP B

To a solution of 2.4 g (4.8 mmoles) of 1-(1-carboxy-2-methylprop-2-enyl)-3-phenoxyacetamido-4-phthalimidothio-azetidin-2-one in 20 ml of tetrahydrofuran was added a solution of 6 mmoles of diazomethane in diethyl ether. The clear solution was treated with acetic acid to remove excess diazomethane and was concentrated to a small volume. After addition of diethyl ether the formed precipitate was filtered off and dried to obtain 1.9 g (3.7 mmoles or 76% yield) of 1-(1-methoxycarbonyl-2-methylprop-2-enyl)-3-phenoxyacetamido-4-phthalimidothio-azetidin-2-one.

PMR: 1.95 (s, 3); 3.57 (s, 3); 4.67 (s, 2); 4.82 (s, 1); 5.09 (s, 1); 5.18 (s, 1); 5.20 (d, 1; J=4.5 Hz); 5.55 (dd, 1; J=4.5 and 8.5 Hz); 6.85 – 7.47 (m, 5); 7,86 (s, 4); 8.28 (d, 1; J=8.5 Hz).

IR (KBr): 3340, about 1780, 1770, 1740, 1720, 1670, 1290 and 1060 cm$^{-1}$.

STEP C

To a solution of 1-(1-methoxycarbonyl-2-methylprop-2-enyl)-3-phenoxyacetamido-4-phthalimidothio-azetidin-2-one 3.6 g (7 mmoles) in 230 ml of 1,2- dichloroethane were added 5 ml of propylene oxide and 1.9 g (10.5 mmoles) of N-bromosuccinimide. The mixture was irradiated under nitrogen for 2 hours at 14° C with a Hanovia TQ 150 mercury high pressure lamp using a Pyrex filter. After washing twice with 150 ml of a 0.067 molar aqueous potassium phosphate solution buffered to pH 5.8, washing twice with 100 ml of water, drying and treating with decolorizing charcoal, the reaction mixture was concentrated. After adding a mixture of ethyl acetate, diethyl ether and n-hexane, the precipitate was chromatographed on silica gel (methylene chloride ethyl acetate 9:1 (v/v) to obtain 1.3 g (2.4 mmoles; 34% yield) of 1-(1-methoxycarbonyl-2-bromomethylprop-2-enyl)-3-phenoxyacetamido-4-phthalimidothio-azetidin-2-one.

PMR: 3.60 (s, 3); 4.23 (s, 2); 4.65 (s, 2); 5.20 (s, 1); 5.24 (d, 1; J=4.5 Hz); 5.41 (s, 1); 5.45 (dd, 1; J=4.5 and 8.5 Hz); 5.65 (s, 1); 6.84 – 7.47 (m, 5); 7.85 (s, 4); 8.23 (d, 1; J=8.5 Hz).

IR (KBr): 3330, 1785, 1745, 1720, 1680, 1600, 1530 and 1500cm$^{-1}$.

EXAMPLE 7

1-(1-n-butoxycarbonyl-2-bromomethylprop-2-enyl)-3-phenoxyacetamido-4-phthalimidothio-azetidin-2-one

STEP A

A mixture of 27 g (64 mmoles) of the n-butyl ester of phenoxymethylpenicillin-S-sulfoxide, 43 g (196 mmoles) of N-trimethylsilylphthalimide and 70 ml of dimethylacetamide was heated with stirring for 10 hours at 105° C and after cooling to room temperature, the reaction mixture was poured into a cold mixture of 200 ml of ethyl acetate, 250 ml of water, 100 g of ice and 2 ml of a 4 N hydrochloric acid solution. After filtering off the formed precipitate (phthalimide), the organic layer of the filtrate was separated, concentrated in vacuo and filtered. After triturating the filtrate with diethyl ether, the crude material was dissolved in 75 ml of acetone, treated with charcoal and concentrated to a small volume. After adding diethyl ether, 10.6 g (19 mmoles; 30% yield) of 1-(1-n-butyloxycarbonyl-2-methylprop-2-enyl)-3-phenoxyacetamido-4-phthalimidothio-azetidin-2-one was obtained.

PMR: 0.70 - 1.85 (m, 7); 1.98 (s, 3); 4.05 (t, 2; J=6 Hz); 4.67 (s, 2); 4.86 (s, 1); 5.11 (s, 1); 5.19 (s, 1); 5.24 (d, 1; J=4.7 Hz); 5.51 (dd, 1; J=4.7 and 8.5 Hz); 6.86 – 7.47 (m, 5); 7.84 (s, 4); 8.11 (d, 1; J=8.5 Hz).

IR (KBr): about 3320, 2960, 1785, 1765, 1740, 1715, 1670, 1530 and 1280 cm$^{-1}$.

M.S.: M$^+$ 551.

STEP B

A mixture of 2.7 g (5 mmoles) of 1-(1-n-butyloxycarbonyl-2-methylprop-2-enyl)-3-phenoxyacetamido-4-phthalimidothio-azetidin-2-one, 200 ml of 1,2-dichloroethane, 1,4 g (5 mmoles) of 1,3-dibromo-5,5-dimethylhydantoin and 3 ml of propylene oxide was irradiated under nitrogen for 3 hours at 14° C with a Hanovia TQ 150 mercury high pressure lamp using a Pyrex filter. After concentrating the reaction mixture, the residue was chromatographed over silica gel [toluene -ethyl acetate 5:1 (v/v)] to obtain 300 mg (0.5 mmole) of 1-(1-n-butyloxycarbonyl-2-bromomethylprop-2-enyl)-3-phenoxyacetamido-4-phthalimidothio-azetidin-2-one.

PMR: about 0.70 - 2.00 (m, 7); 4.08 (t, 2; J=6.5 Hz); 4.27 (s, 2); 4.69 (s, 2); 5.23 (s, 1); 5.28 (d, 1; J=4.5 Hz); 5.43 (dd, 1; J=4.5 and 8.5 Hz); 5.45 (s, 1); 5.66 (s, 1); 6.84 – 7.48 (m, 5); 7.84 (s, 4); 8.05 (d, 1; J=8.5 Hz).

IR (KBr): about 3340, 2960, 1780, 1750, 1715, 1600, 1530, 1495 and 1060 cm$^{-1}$.

EXAMPLE 8

1-(1-p-nitrobenzyloxycarbonyl-2-bromomethylprop-2-enyl)-3-phenoxyacetamido-4-phthalimidothio-azetidin-2-one

STEP A

A mixture of 225 g (448 mmoles) of the p-nitrobenzyl ester of phenoxymethylpenicillin-S-sulfoxide, 500 ml of dimethylacetamide, 310 g (1414 mmoles) of N-trimethylsilylphthalimide and 10 ml (66 mmol) of trimethylsilylacetate was stirred for 8 hours at 105° C and after cooling to room temperature, the reaction mixture was poured into a cold mixture of 2 liters of ethyl acetate, 3 liters of water and 25 ml of a 4 N hydrochloric acid solution. After filtering off the formed precipitate consisting of phthalimide and the desired product, the organic layer of the filtrate was separated, concentrated and filtered to obtain a second crop of the same material. The combined raw material was then dissolved in 2.5 liters of hot chloroform, the solution was concentrated to about 600 ml and the precipitated phthalimide was filtered off. By adding diethyl ether to the filtrate, some crude product was obtained. By repeating this procedure several times, a total 104 g (37% yield) of 1-(1-p-nitrobenzyloxycarbonyl-2-methylprop-2-enyl)-3-phenoxyacetamido-4-phthalimidothio-azetidin-2-one was obtained.

PMR: 1.96 (s, 3); 4.69 (s, 2); 4.99 (s, 1); 5.10 (s, 1); 5.19 (s, 1); 5.15 (d, 1; J=4.5 Hz); 5.21 (s, 2); 5.47 (dd, 1; J=4.5 and 8.5 Hz); 6.88 – 7.55 (m, 5); 7.46 (d, 2; J=8.5 Hz); 8.17 (d, 2; J=8.5 Hz); 7.79 (s, 4); 8.07 (d, 1; J=8.5 Hz).

IR (KBr): 3330, 1780, 1769, 1740, 1715, 1672 and 1060 cm$^{-1}$.

STEP B

A mixture of 1.26 g (2 mmoles) of 1-(1p-nitro-benzyloxycarbonyl-2-methylprop-2-enyl)-3-phenoxyacetamido-4-phthalimidothio-azetidin-2-one, 0.71 g (4 mmoles) of N-bromosuccinimide, 50 mg (0.3 mmole) of azoisobutyronitrile and 80 ml of 1,2-dichloroethane was heated in the dark under nitrogen at 70° C for 3 hours. After washing twice with a sodium metabisulfite solution and with water, the reaction mixture was dried and concentrated to a small volume. After treating the residue with hexane, 1.2 g of crude material was isolated which was purified with column chromatography [silica gel, 10:1 (v/v) methylene chloride ethyl acetate] to obtain 0.33 g (0.5 mmole; 23% yield) of 1-(1-p-nitrobenzyloxycarbonyl-2-bromomethylprop-2-enyl)-3-phenoxyacetamido-4-phthalimidothioazetidin-2-one.

PMR: 4.23 (s, 2); 4.66 (s, 2); 5.17 (d, 1; J=4.5 Hz); 5.23 (s, 2); 5.35 (dd, 1; J=4.5 Hz and J=7 Hz); 5.36 (s, 1); 5.42 (s, 1) and 5.63 (s, 1); 6.82 – 7.47 (m, 5); 7.47 (d, 2; J=8.5 Hz); 8.15 (d, 2; J=8.5 Hz); 7.79 (s, 4); 7.98 (d, 1; J=7 Hz).

IR (KBr): about 3450, 1780, 1745, 1715; about 1675, 1522, 1350 and 1055 cm$^{-1}$.

EXAMPLE 9

1-(1-diphenylmethoxycarbonyl-2-bromomethylprop-2-enyl)-3-phenoxyacetamido-4-phthalimidothio-azetidin-2-one

STEP A

A mixture of 41 g (77 mmoles) of the diphenylmethyl ester of phenoxymethylpenicillin-S-sulfoxide, 50 g (228 mmoles) of N-trimethylsilylphthalimide and 90 ml of N,N-dimethylacetamide was heated for 8 hours at 102° C during which a white precipitate was formed. After standing overnight, the fine needles were filtered off, washed with acetone and dried to obtain 26.3 g (52% yield) of 1-(1-diphenylmethoxycarbonyl-2-methylprop-2-enyl)-3-phenoxyacetamido-4-phthalimidothio-azetidin-2-one.

PMR: (DMSO - d 6): 1.85 (s, 3); 4.72 (s, 2); 4.97 (s, 1); 5.03 (s, 2); 5.17 (s, 1); 5.18 (dd, 1; J=5 Hz and J=7.5 Hz); 5.38 (d, 1; J=5 Hz); 6.88 (s, 1); 6.93 – 7.59 (m, 5); 7.39 (s, 5); 7.42 (s, 5); 7.78 (s, 4); 9.25 (d, 2; J=7.5 Hz).

IR (KBr): 3360, 3090, 3060, 3050, 1792, 1770, 1720, 1675, 1603, 1590, 1530, 1498 and 1242 cm$^{-1}$.

STEP B

A mixture of 5.6 g (8 mmoles) of 1-(1-diphenylmethoxycarbonyl-2-methylprop-2-enyl)-3-phenoxyacetamido-4-phthalimidothio-azetidin-2-one, 2.8 g (16 mmoles) of N-bromosuccinimide, 150 mg of benzoyl peroxide and 350 ml of 1,2-dichloroethane was heated in the dark under nitrogen at 80° C for 2.5 hours. After washing with water, drying and concentrating of the reaction mixture, n-hexane was added to the residue to obtain 3 g of crude material which was chromatographed with silica gel [toluene-ethyl acetate 7:1 (v/v)] to obtain 630 mg (0.8 mmole) of 1-(1-diphenylmethoxycarbonyl-2-bromomethylprop-2-enyl)-3-phenoxyacetamido-4-phthalimidothio-azetidin-2-one.

PMR (DMSO - d 6): 4.40 (s, 2); 4.71 (s, 2); 5.16 (dd, 1; J=5 Hz and 7 Hz); 5.27 (s, 1); 5.63 (s, 1); 5.40 (s, 1); 5.41 (d, 1; J=5 Hz); 6.88 (s, 1); 6.91-7.56 (m, 5); 7.38 (s, 10); 7.93 (s, 4); 9.27 (d, 1; J=7Hz).

IR (KBr): 3360, 1790, 1775, 1750, 1720, 1675, 1530, 1170, 950 and 920 cm$^{-1}$.

EXAMPLE 10

1-(1-p-nitrobenzyloxycarbonyl-2-bromomethylprop-2-enyl)-3-phenoxyacetamido-4-phthalimidothio-azetidin-2-one The procedure of Step B of Example 8 was repeated with the exception that 40 mg of benzoyl peroxide instead of 50 mg of azoisobutyronitrile was used and mainly one product, 1-(1-p-nitrobenzyloxycarbonyl-2-bromomethylprop-2-enyl)-3-phenoxyacetamido-4-phthalimidothio-azetidin-2-one, was formed.

The procedure of Step B of Example 8 was repeated with the exception that 80 ml of benzene instead of 80 ml of 1,2-dichloroethane were used and mainly one product, 1-(1-p-nitrobenzyloxycarbonyl-2-bromomethylprop-2-enyl)-3-phenoxyacetamido-4-phthalimidothio-azetidin-2-one, was formed.

The procedure of Step B of Example 8 was repeated but with 0.47 g of N-bromosuccinimide (instead of 0.71 g) and using chloroform instead of 1,2-dichloroethane and there was obtained mainly one product, 1-(1-p-nitrobenzyloxycarbonyl-2-bromomethylprop-2-enyl)-3-phenoxyacetamido-4-phthalimidothio-azetidin-2-one.

EXAMPLE 11

120 mg (2 mmoles) of acetic acid and 250 mg (2.5 mmoles) of dry potassium acetate were added to a solution of 262 mg (0.5 mmole) of 1-(1-methoxycarbonyl-2-bromomethylprop-2-enyl)-3-phenylacetamido-4-succinimidothio-azetidin-2-one in 15 ml of dimethylformamide and after stirring for one hour under nitrogen at 25° C, the starting material was converted into a mixture of two compounds according to thin layer chromatography. The reaction mixture was then poured into a mixture of 150 ml of water and 50 ml of ethyl acetate. After separating the layers and extracting the water layer twice with 50 ml portions of ethyl acetate, the combined organic layers were washed and treated with diethyl ether to obtain 125 mg (64% yield) of a mixture of the methyl esters of $\Delta^3$- and $\Delta^2$-benzylcephalosporanic acids.

PMR: $\Delta^3$-compound: 2.07 (s, 3); 3.25 and 3.61 (ABq, 2; J=18.5 Hz); 3.65 (s, 2); 3.85 (s, 3); 4.93 (d, 1; J=4.5Hz); 4.76 and 5.09 (ABq, 2; J=13 Hz); 5.79 (dd, 1; J=4.5 Hz and J=8.5 Hz); about 6.40 (d, 1; J=8.5 Hz); 7.32 (s, 5).

$\Delta^2$-compound: 2.07 (s, 3); 3.65 (s, 2); 3,80 (s, 3); 4.62 (s, 2); 4.99 (s, 1); 5.21 (d, 1; J=4 Hz); 5.62 (dd, 1; J=4 Hz and J=8.5 Hz); about 6.40 (s, 2); 7.32 (s, 5).

The procedure was repeated using 210 mg of sodium acetate instead of potassium acetate to obtain a mixture of the methyl esters of $\Delta^2$- and $\Delta^3$- benzylcephalosporanic acids. The procedure was repeated again using 190 mg of ammonium acetate instead of potassium acetate to obtain a mixture of the methyl esters of $\Delta^2$- and $\Delta^3$-benzylcephalosporanic acids. Again the procedure was repeated using 135 mg of tetramethylammonium acetate instead of potassium acetate to obtain a mixture of the methyl esters of $\Delta^2$- and $\Delta^3$-benzylcephalosporanic acids.

EXAMPLE 12

2 g (20 mmoles) of potassium acetate were added to a solution of 2 g (3.8 mmoles) of 1-(1-methoxycarbonyl-2-bromomethylprop-2-enyl)-3-phenylacetamido-4-succinimidothio-azetidin-2-one in 50 ml of dry acetone under nitrogen and the mixture was boiled for one hour. According to thin layer chromatography, the reaction mixture contained a mixture of the methyl esters of $\Delta^3$- and $\Delta^2$-benzylcephalosporanic acids. The solvent was removed in vacuo and the residue was purified by column chromatography [silica gel; 8:1 (v/v) methylene chloride-acetone] to obtain 50 mg of the methyl ester of $\Delta^2$-benzylcephalosporanic acid. The structure was confirmed by PMR and IR spectroscopy.

EXAMPLE 13

A mixture of 172 mg (0.3 mmole) of 1-(1-methoxycarbonyl-2-bromomethylprop-2-enyl)-3-phenylacetamido-4-phthalimidothio-azetidin-2-one, 10 ml of dimethylformamide, 170 mg (2.8 mmoles) of acetic acid and 150 mg (1.5 mmole) of potassium acetate was stirred for 0.5 hour under nitrogen at 25° C and after pouring the reaction mixture into a mixture of 30 ml of water and 15 ml of ethyl acetate, the layers were separated and the water layer extracted with some more ethyl acetate. After washing the combined organic layers with water, drying and treating with charcoal, the ethyl acetate was evaporated and the residue was extracted with a mixture of benzene and ethyl acetate. This extract was chromatographed [silica gel; benzene-ethyl acetate 6:1 (v/v)] to obtain 20 mg (0.05 mmole; 17% yield) of the $\Delta^3$-benzylcephalosporin methyl ester and 30 mg (0.074 mmole; 25% yield) of the $\Delta^2$-benzylcephalosporin methyl ester. The structures were confirmed by PMR and IR spectroscopy.

EXAMPLE 14

222 mg (0.3 mmole) of 1-(1-diphenylmethoxycarbonyl-2-bromomethylprop-2-enyl)-3-phenoxyacetamido-4-phthalimidothio-azetidin-2-one were added to a solution of 150 mg (1.5 mmoles) of potassium acetate in 150 mg of acetic acid and 12 ml of dimethylformamide. After stirring for 1.5 hours under nitrogen at room temperature, the reaction mixture was poured into a mixture of 100 ml of water and 100 ml of ethyl acetate. Concentration of the organic layer and evaporation of the solvent gave a crude mixture of the diphenylmethyl esters of $\Delta^2$- and $\Delta^3$-phenoxymethylcephalosporanic acids, according to thin layer chromatography. A sample was further separated by preparative thin layer chromatography (3:1 toluene-ethyl acetate).

PMR: $\Delta^3$-compound: 2.02 (s, 3); 3.45 (s, br, 2); 4.55 (s, 2); 4.77 and 5.06 (ABq, 2; J=12 Hz); 5.01 (d, 1; J=4.5 Hz); 5.93 (dd, 1; J=4.5 and 9 Hz); about 6.80 – 7.47 (m, 6); about 7.35 (s, 10).

PMR: $\Delta^2$-compound: 1.95 (s, 3); 4.55 (s, 2); 4.57 (s, 2); 5.01 (s, 1); 5.25 (d, 1; J=4 Hz); 5.70 (dd, 1; J=4 and 9Hz); 6.42 (s, br, 1); 6.78 – 7.54 (m, 6); 7.35 (s, 10).

EXAMPLE 15

426 mg (0.6 mmoles) of 1-(1-p-nitrobenzyloxycarbonyl-2-bromomethylprop-2-enyl)-3-phenoxyacetamido-4-phthalimidothioazetidin-2-one were added to a solution of 300 mg (3 mmoles) of potassium acetate in 300 mg (4.8 mmoles) of acetic acid and 25 ml of dimethylformamide. After stirring for two hours under nitrogen at room temperature and standing overnight at 4° C, 75 ml of ethyl acetate were added. Ater filtering off the precipitated phthalimide, the filtrate was washed twice with a 0.2 molar aqueous solution of sodium acetate and acetic acid buffered to pH 4.6, treated with charcoal, dried and concentrated in vacuo. The residue was chromatographed on silica gel [benzene-acetone 95:5 (v/v)] to obtain 35 mg (0. 065 mmole) of the p-nitrobenzyl ester of $\Delta^3$-phenoxyacetamidocephalosporanic acid and 40 mg (0.075 mmole) of the corresponding $\Delta^2$compound.

PMR: $\Delta^2$-compound: 2.03 (s, 3); 4.51 and 4.74 (ABq, 2; J=13.5 Hz); 4.56 (s, 2); 5.13 (s, 1); 5.28 (d, 1; J=3.7 Hz); 5.31 (s, 2); 5.56 (dd, 1; J=3.7 and 9 Hz); 6.46 (s, 1); 6.78–7.47 (m, 5); 7.45 (d, 1; J=9 Hz); 7.51 (d, 2; J=8.5 Hz); 8.25 (d, 2; J=8.5 Hz).

PMR: $\Delta^3$-compound: 2.09 (s, 3); 3.34 and 3.69 (ABq, 2; J=19 Hz); 4.58 (s, 2); 4.77 and 5.18 (ABq, 2; J=13.5 Hz); 5.04 (d, 1; J=4.8 Hz); 5.37 (s, 2); 5.94 (dd, 1; J=4.8 Hz and 9.2 Hz); 6.82 – about 7.50 (m, 5); 7.23 (d, 1; J=9.2 Hz); 7.59 (d, 2; J=8.8 Hz); 8.24 (d, 2; J=8.8 Hz).

The procedure was repeated with various other solvents instead of dimethylformamide. In some cases, no acetic acid was added to the reaction mixture. Sometimes the reaction was carried out at a higher temperature than that used during the reaction described above. The various reaction conditions are listed in the table here below.

| Solvent | Acetic acid present | Temperature |
| --- | --- | --- |
| acetonitrile | − | 60° C |
| acetone | − | 60° C |
| dimethoxy ethane | − | 60° C |
| methyl isobutyl ketone | − | 60° C |
| hexamethylphosphoric triamide | + | 25° C |
| dimethylsulfoxide | + | 25° C |
| dimethylacetamide | + | 25° C |

In all cases a mixture of the p-nitrobenzyl esters of $\Delta^2$- and $\Delta^3$-phenoxyacetamidocephalosporanic acids was obtained.

Various modifications of the compounds and the processes of the invention may be made without departing from the spirit or scope thereof and it is to be understood that the invention is to be limited only as defined in the appended claims.

We claim:
1. An azetidine compound of the formula

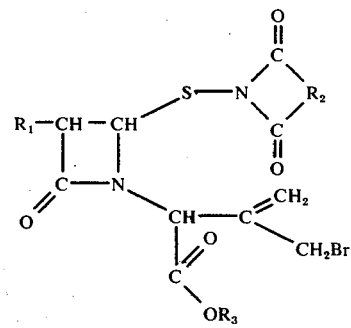

wherein $R_1$ is a penicillin acylamido group, $R_2$ is selected from the group consisting of

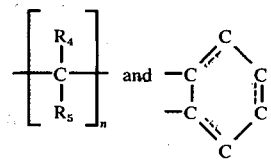

wherein $R_4$ and $R_5$ are individually selected from the group consisting of hydrogen, lower alkyl and lower alkenyl, n is 2 and — in the case when $R_2$ is a phenyl this group may carry one to four substituents selected from the group consisting of halogen, lower alkyl, lower alkenyl and phenyl, and $R_3$ is lower alkyl optionally substituted with 1 or 2 phenyls which phenyl groups may be substituted with nitro and the dotted lines of the second formula indicate the optional presence of double bonds.

2. A compound of claim 1 wherein $R_1$ is selected from the group consisting of phenylacetamido and phenoxyacetamido.

3. A compound of claim 1 wherein the group

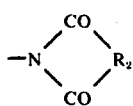

is selected from the group consisting of succinimids and phthalimido.

4. A compound of claim 1 wherein $R_3$ is selected from the group consisting of methyl, butyl, diphenylmethyl and p-nitrobenzyl.

5. A compound of claim 1 which is 1-(1-methoxycarbonyl-2-bromomethylprop-2-enyl)-3-phenylacetamido-4-succinimidothio-azetidin-2-one.

6. A compound of claim 1 which is 1-(1-methoxycarbonyl-2-bromomethylprop-2-enyl)-3-phenylacetamido-4-phthalimidothio-azetidin-2-one.

7. A compound of claim 1 which is 1-(1-methoxycarbonyl-2-bromomethylprop-2-enyl)-3-phenoxyacetamido-4-phthalimidothio-azetidin-2-one.

8. A compound of claim 1 which is 1-(1-n-butyloxycarbonyl-2-bromomethylprop-2-enyl)-3-phenoxyacetamido-4-phthalimidothio-azetidin-2-one.

9. A compound of claim 1 which is 1-(1-p-nitrobenzyloxycarbonyl-2-bromomethylprop-2-enyl)-3-phenoxyacetamido-4-phthalimidothio-azetidin-2-one.

10. A compound of claim 1 which is 1-(1-diphenylmethoxycarbonyl-2-bromomethylprop-2-enyl)-3-phenoxyacetamido-4-phthalimidothio-azetidin-2-one.

* * * * *